US007375095B2

(12) United States Patent
Oku et al.

(10) Patent No.: US 7,375,095 B2
(45) Date of Patent: May 20, 2008

(54) SUGAR DERIVATIVE

(75) Inventors: Kazuyuki Oku, Okayama (JP); Naoki Kudo, Okayama (JP); Shigeharu Fukuda, Okayama (JP)

(73) Assignee: Kabashiki Kaisha Hayashibara Seibutsu Kagaku, Okayama (JP)

( * ) Notice: Subject to any disclaimer, the term of this patent is extended or adjusted under 35 U.S.C. 154(b) by 316 days.

(21) Appl. No.: 10/495,975

(22) PCT Filed: Nov. 19, 2002

(86) PCT No.: PCT/JP02/12065

§ 371 (c)(1),
(2), (4) Date: May 19, 2004

(87) PCT Pub. No.: WO03/044032

PCT Pub. Date: May 30, 2003

(65) Prior Publication Data

US 2004/0254367 A1    Dec. 16, 2004

(30) Foreign Application Priority Data

Nov. 20, 2001  (JP) ............................... 2001-355077

(51) Int. Cl.
*A01N 43/54* (2006.01)
*A01N 43/04* (2006.01)
*A61K 31/715* (2006.01)
*C07G 17/00* (2006.01)
*C07H 1/00* (2006.01)

(52) U.S. Cl. ........................... 514/54; 536/123; 514/61
(58) Field of Classification Search .................. 514/54, 514/61; 536/123
See application file for complete search history.

(56) References Cited

U.S. PATENT DOCUMENTS 5,786,196 A *  7/1998  Cote et al. ................... 435/208
5,889,179 A    3/1999  Cote et al.
2004/0236097 A1* 11/2004  Aga et al. .................... 536/123

FOREIGN PATENT DOCUMENTS

| EP | 1 229 112 A1 | 8/2002 |
| EP | 1 284 286 A1 | 2/2003 |
| EP | 1 360 988 A1 | 11/2003 |
| EP | 1 380 595 A1 | 1/2004 |
| WO | WO 01/90338 A1 | 11/2001 |
| WO | WO 02/10361 A1 | 2/2002 |
| WO | WO 02/057011 A1 | 7/2002 |
| WO | WO 02/072594 A1 | 9/2002 |

OTHER PUBLICATIONS

The Merck Index, 13th Edition, p. 794, monograph for "Glucose" © 2001 by Merck & Co., Inc.*

Hawley's Condensed Chemical Dictionary, 13th Edition, pp. 540-541, entry for "Glucose" © 1997 by Van Nostrand Reinhold.*
M. Yalpani, Polysaccharides: Syntheses, Modifications and Structure/Property Relations, In: Studies in Organic Chemistry, pp. 36:234-299 (1988).
Côté et al., The Hydrolytic and Transferase Action of Alternanase on Oligosaccharides, *Carbohydrate Research*, 332:373-379 (2001).
Boger, J., et al, "203. Cyclodextrin chemistry. Selective modification of all primary hydroxyl groups of α- and β-cyclodextrins", Helvetica Chimica Acta. (1978). vol. 61, pp. 2190-2218.
Breslow, Ronald and Anthony Czarnik, "Transaminations by Pyridoxamines selectively attached at C-3 in β-cyclodexrin" J. Am. Chem. Soc. (1983. vol. 103, pp. 1390-1391.
Cote, Gregory and Peter Biely, "Enzymically produced cyclic α-1,3-linked and α-1,6-linked oligosaccharides of D-glucose", Eur. J. Biochem. (1994). vol. 226, pp. 641-648.
Harada, Aakira, "Design and synthesis of macromolecular systems consisting of cyclodextrins and polymers", J. Michl (ed.), Molecular Chemistry. (1997).Kluwer Academic Publishers. Netherlands, pp. 361-370.
Hedges, Allan, "Industrial applications of cyclodextrins", Chem. Rev. (1998). vol. 98, pp. 2035-2044.

(Continued)

*Primary Examiner*—Zachary C Tucker
(74) *Attorney, Agent, or Firm*—Browdy and Neimark, P.L.L.C.

(57) ABSTRACT

For extending the uses of a compound represented by Chemical formula 1, the object of the present invention is to provide a derivative of cyclic tetrasaccharide whose physicochemical properties are changed from those of cyclic tetrasaccaride, a composition comprising the same, and a process for producing the same. The present invention solves the above object by providing a derivative of cyclic tetrasaccharide, which is produced by the steps of reacting a compound represented by Chemical formula 1 with a reactive reagent and substituting one ore more hydroxyl groups with substituents except hydroxyl group and O-glycosyl group; a composition comprising the same; and a process for producing the derivative of cyclic tetrasaccharide.

Chemical formula 1

7 Claims, No Drawings

OTHER PUBLICATIONS

Hirst, E. and Elizabeth Percival, "Methyl Ethers of Mono- and Disaccharides", Whistler et al (eds.) Methods In Carbohydrate Chemistry. (1963). Academic Press Inc., New York. 145-151.

Ichikawa, et al, "Simple preparation of multi-valent cyclodextrin-carbohydrate conjugates", Tetrahedron: Asymmetry. (2000). vol. 11, pp. 389-392.

Ikeda, et al, "Modifications of the secondary hydroxyl side of α-cyclodextrin and NMR studies of them", Tetrahedron Letters. (1990). vol. 31, No. 35, pp. 5045-5048.

Khan, et al, "Methods for selective modifications of cyclodextrins", Chem. Rev. (1998). vol. 98, pp. 1977-1996.

Komiyama, "Kagaku (Science)" (in Japanese), (1989), vol. 59, No. 2, pp. 105-112.

Lee, Cheang Kuan, "Trehalose", C.K. Lee (ed) Developments In Food Carbohydrate-2. (1980). Applied Science Publishers Ltd. Essex, GB. Chapter 1, pp. 1-89.

Murakami, et al, "Synthesis and chiral recognition property of 3-acetylamino-3-deoxy-8-cyclodextrin", Chemistry Letters. (1988), No. 3, pp. 553-556.

Suzuki, et al, "Ferrocene-appended cyclodextrins. The effects of temperature, organic solvent, length of spacer, and cavity size in the complexation behavior", Bull. Chem. Soc. Jpn. (1993). vol. 66, No. 5, pp. 1472-1481.

Szejtli, Jozsef, "Utilization of cyclodextrins in industrial products and processes", J. Mater. Chem. (1997). vol. 7, No. 4, pp. 575-587.

Szeja, Wieslaw, "Convenient synthesis and application of sucrose sulfates", Frieder Lichtenthaler (ed.), Carbohydrates as Organic Raw Materials. (1990). VCH, Weineim, Chapter 5, pp. 117-125.

Ueno, A., et al, "Host-guest complexation of ferrocene-appended β-cyclodextrin in organic solvents", Makromol. Chem., Rapid Commun. (1985). vol. 6, pp. 231-233.

Ueno, Akihiko and Ronald Bewslow, "Selective sulfonation of a secondary hydroxyl group of β-cyclodextrin", Tetrahedron Letters (1982). vol. 23, No. 34, pp. 3451-3454.

Yoshimoto, K. et al, "Chemical and biochemical studies on carbohydrate esters. XIII. Synthesis of 6-O-, 6,6'- Di-O- and 4,6,4',6'-Tetra-O-stearoyl-α,α-trehaloses" Chem. Pharm. Bull. (1982). vol. 30, No. 4, pp. 1169-1174.

* cited by examiner

US 7,375,095 B2

SUGAR DERIVATIVE

TECHNICAL FIELD

The present invention relates to novel derivatives of cyclic tetrasaccharide, compositions comprising the same, and processes for producing the derivatives of cyclic tetrasaccharide.

BACKGROUND ART

A cyclic tetrasaccharide, having a structure composed of four glucose molecules bound together via alternating α-1,3-glucosidic linkage and α-1,6-glucosidic linkage, i.e., a compound having a structure of cyclo{→6)-α-D-glucopyranosyl-(1→3)-α-D-glucopyranosyl-(1→6)-α-D-glucopyranosyl-(1→3)-α-D-glucopyranosyl-(1-}, represented by Chemical formula 1 (hereinafter, briefly called as "cyclotetrasaccharide"), and a process for producing the saccharide by allowing a hydrolytic enzyme, alternanase, to act on a polysaccharide, alternan, were reported by Gregory L. Cote et al. in *European Journal of Biochemistry*, Vol. 226, pp. 641-648, 1994. However, the industrial production of cyclotetrasaccharide by the above process has been difficult because of the expensiveness of material alternan. Recently, as disclosed in International Publication Nos. WO 01/90,338 (international application No. PCT/JP01/04,276) and WO 02/10,361 (international application No. PCT/JP01/06,412), applied for by the same applicant as the present invention; a process for producing cyclotetrasaccharide, using both enzymes originated from microorganisms and inexpensive starch as a material, was established. Therefore, the process enables us to produce cyclotetrasaccharide industrially, and the uses of the saccharide are now developing.

Chemical formula 1

Chemical formula 1

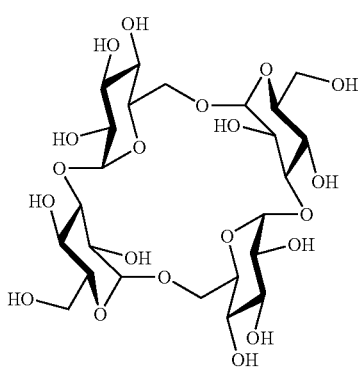

In order to extend the uses of cyclotetrasaccharide, it is meaningful to produce novel derivatives of cyclotetrasaccharide, having different physical properties from those of cyclotetrasaccharide. As reports referred to the derivatives of cyclotetrasaccharide, Japanese Patent Application No. 67,282/2001 (title of the invention, "Branched cyclic tetrasaccharide, its preparation and uses") and U.S. Pat. No. 5,889,179 disclosed the derivative having a structure of glucosyl-cyclotetrasaccharide, i.e., branched cyclotetrasaccharide. Since the derivatives of cyclotetrasaccharide described in those are produced by binding O-glycosyl groups with cyclotetrasaccharide by using O-glycosyl group-transferring enzymes, the resulting derivatives have only O-glycosyl groups. Therefor, it is restricted to change the physical properties of cyclotetrasaccharide by binding an O-glycosyl group(s) with cyclotetrasaccharide.

The object of the present invention is to provide derivatives of cyclotetrasaccharide, having different physical properties from those of cyclotetrasaccharide, compositions comprising the same, and processes for producing the derivatives of cyclotetrasaccharide.

DISCLOSURE OF INVENTION

In the course of extensive studies, the present inventors newly found that derivatives of cyclotetrasaccharide represented by Formula 1, cyclotetrasaccharide whose hydroxyl groups were substituted by other substituents, can be obtained by allowing reactive reagents to act on cyclotetrasaccharide without using enzymatic reaction system with generally known various saccharide-related enzymes such as cyclodextrin glucanotransferase, α-galactosidase, β-galactosidase, lysozyme, other glycosyltransferases, other saccharide hydrolases, and saccharide phosphorylases. The present inventors found that various substituents could be specifically introduced into cyclotetrasaccharide in addition to O-glycosyl group or modified O-glycosyl group, which could be introduced by conventional enzymatic systems, and physical properties of cyclotetrasaccharide could be arbitrarily changed by the above reaction, and accomplished the present invention. According to the present invention, physical properties of cyclotetrasaccharide such as sweetness, less fermentability, low cariogenicity, low caloric property, osmotic pressure-controlling property, excipiency, gloss-imparting property, moisture-retaining property, viscosity, syneresis-preventing property, solidification-preventing property, inclusion complex-forming property, flavor-keeping property, stability, property for preventing the crystallization of other saccharide, starch-retrogradation-preventing property, protein-denaturation-preventing property, lipid-deterioration-preventing property, stability to acids, non-aminocarbonyl-reactivity, dielectricity, polarizability, and electric-conductivity can be arbitrarily changed. For example, a saccharide derivative, having a strong hydrophobic substituent(s), has a lipophilic property which is not inhered to intact cyclotetrasaccharide. Since a derivative of cyclotetrasaccharide, having a highly reactive substituent, has a superior binding ability with cyclotetrasaccharide or other organic compounds, it can be advantageously used for polymerizing cyclotetrasaccharides or binding with other organic compounds. The physical properties of other organic compounds can be changed by allowing the organic compounds to bind with cyclotetrasaccharide by using the above derivatives.

Formula 1

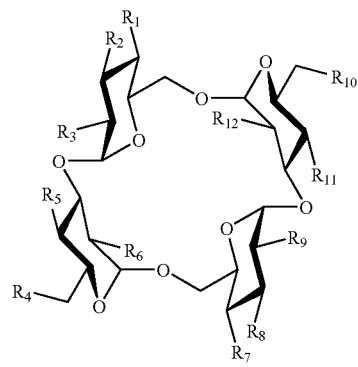

In the above formula, $R_1$ to $R_{12}$ mean optional substituents, but one or more of them are those except hydroxyl group and O-glycosyl group.

The present invention solves the objects by the above method. The present invention provides the derivatives of cyclotetrasaccharide whose physical properties such as lipophilic property and binding property are changed from those of cyclotetrasaccharide by substituting hydroxyl groups of cyclotetrasaccharide with other substituents except hydroxyl groups and O-glycosyl groups.

The present invention also provides the uses of the derivatives of cyclotetrasaccharide whose physical properties such as lipophilic property and binding property are changed from those of cyclotetrasaccharide.

The present invention further provides processes for producing the derivatives of cyclotetrasaccharide whose physical properties such as lipophilic property and binding property are changed from those of cyclotetrasaccharide.

BEST MODE FOR CARRYING OUT THE INVENTION

A derivative of cyclotetrasaccharide as referred to as in the present invention means a derivative produced by substituting one or more hydroxyl groups of cyclotetrasaccharide with other substituents except hydroxyl groups and O-glycosyl groups by reacting a reactive reagent with cyclotetrasaccharide (hereinafter, briefly called "a derivative of cyclotetrasaccharide"). An O-glycosyl group as referred to as in the present invention means O-glycosyl group which can be substituted with hydroxyl group of cyclotetrasaccharide, and that modified in an acceptable range of being substituted by an enzymatic reaction system. A reaction system, used for producing the derivatives of cyclotetrasaccharide of the present invention, is a chemical reaction system using a reactive reagent and not an enzymatic reaction system. Therefore, it is possible to introduce modified O-glycosyl groups, which are hardly introduced by conventional enzymatic reaction systems, into cyclotetrasaccharide. As chemical reactions, esterification, etherification, sulfonation, amination, etc., which are conventionally used for producing derivatives of saccharide such as starch, can be used. Specifically, methods for chemically modifying cyclodextrins, cyclic saccharides constructed by 6-8 glucose molecules, can be widely used. For example, such methods described in Joshua Boger et al., *Helvetica Chimica Acta*, Vol. 61, pp. 2190-2218, 1978; C. K. Lee, *Development in Food Carbohydrate*, pp. 1-89, 1980, published by Applied Science Publishers; K. Yoshimoto et al., *Chemical and Pharmaceutical Bulletin*, Vol. 30, No. 4, 1, pp. 1169-1174, 1982; *Carbohydrates as Organic Raw Material*, 1991, published by VCH; and *Methods in Carbohydrate Chemistry II*, 1963, published by Academic Press; are all usable in the present invention and can be arbitrarily selected according to the objective derivative of cyclotetrasaccharide.

A hydrocarbon group as referred to as in the present invention means a group constructed by one or more carbon atoms and hydrogen atoms, and includes saturated and unsaturated hydrocarbon groups. For example, aliphatic hydrocarbon groups having carbon number 1-18 such as methyl, ethyl, ethynyl, propyl, isopropenyl, 1-propenyl, l-propynyl, 2-propenyl, butyl, isobutyl, s-butyl, t-butyl, vinyl, 1,3-butadienyl, 2-butenyl, pentyl, isopentyl, neopentyl, t-pentyl, 1-methylpentyl, 2-methylpentyl, 2-pentenyl, 2-penten-4-ynyl, hexyl, isohexyl, 5-methylhexyl, heptyl, and octyl; aliphatic cyclic hydrocarbon groups such as cyclopropyl, cyclobutyl, cyclopentyl, cyclohexyl, and cyclohexenyl; mono- or polycyclic aromatic hydrocarbon groups having a benzene ring as a basic frame such as phenyl and naphthyl; can be listed as hydrocarbon groups.

A substituent, having oxygen except hydroxyl group and O-glycosyl group, as referred to as in the present invention means every substituent having oxygen except hydroxyl group and O-glycosyl group and usually means substituents constructed by oxygen atom and other atoms: for example, hydrogen, carbon, nitrogen, sulfur, halogen, etc. For example, esters of saturated, unsaturated, branched or linear fatty acids such as caproic acid, caprylic acid, capric acid, lauric acid, myristic acid, palmitic acid, stearic acid, arachic acid, behenic acid, lignoceric acid, zoomaric acid, oleic acid, linoleic acid, linolenic acid, gadoleic acid, erucic acid, and selacoleic acid; ester of carboxylic acids such as acetic acid (acetyl), propionic acid (propionyl), and benzoic acid (benzyl); sulfuric ester, phosphoric ester; ether form of alkyl alcohol having carbon number of 1-18 (alkoxyl group) such as methanol (methoxy), ethanol (ethoxy), and propanol (propoxy); ether form of aromatic alcohol such as benzyl alcohol and phenol; functional group having oxygen atoms except hydroxyl groups such as carboxyl, aldehyde, ketone; hydrocarbon group having functional group(s) such as carboxyl, aldehyde, keto, and hydroxyl; and various oxide.

A substituent having nitrogen as referred to as in the present invention means every substituent having one or more nitrogen atoms and usually means a substituent constructed by nitrogen atom(s) and other atoms: for example, a functional group such as amino, hydroxylamino, oxime, carbamide, carbamic acid ester, thiocarbamic acid O-ester, thiocarbamic acid S-ester, imino, azirine, nitro, nitroso, azide, diazo, nitrile, isonitrile, cyano, isocyanate, isothiocyanate, and cyanuric chloride; substituents having those; and various nitrogen compounds.

A substituent having sulfur as referred to as in the present invention means every substituent having one or more sulfur atoms and usually means a substituent constructed by sulfur atom and other atoms: for example, a functional group such as mercapto, sulfonyl, sulfonic acid, sulfide, disulfide, sulfoxide, sulfonyl imido, sulfen, sulfine, thiolsulfinato, thiolsulfonato, sulfilimine, and p-toluene sulfonyl; substituent having those; and various sulfur compounds.

A substituent having halogen as referred to as in the present invention means every substituent having one or more halogen atoms, and usually means a substituent constructed by halogen atom(s) and other atoms: for example, functional group such as fluorine, chlorine, bromine, and iodine; substituents having those; and various halide.

A derivative of cyclotetrasaccharide of the present invention can be produced by the steps of dissolving, suspending or soaking cyclotetrasaccharide in a solvent mentioned after, adding a reactive reagent as a substituent donor, if necessary, with a catalyst, and reacting under suitable conditions (such as temperature, time, pH, and pressure) while mixing or stirring by a suitable method. The resulting derivative of cyclotetrasaccharide can be purified by removing remaining reactive reagent, solvent and/or catalyst using suitable purification procedures.

For example, a hydrocarbon solvent such as propane, butane, pentane, hexane, isohexane, heptane, isoheptane, isooctane, benzene, rubber volatile oil, soybean volatile oil, mineral spirit, cleaning solvent, petroleum ether, petroleum benzene, ligroin, kerosene, cyclohexane, methylcyclohexane, benzene, benzol, toluene, toluol, xylene, xylol, ethylbenzene, cumene, mesitylene, light-solvent naphtha, heavy-solvent naphtha, tetraline, decaline, creosote oil, and turpentine oil; a halogen solvent such as methyl chloride, methylene chloride, chloroform, carbon tetrachloride, dichloro-difluoro-methane, ethyl chloride, 1,2-dichloroethane, 1,2-dibromoethane, tetrachloroethane, dichloroethylene, trichloroethylene, perchloroethylene, dichloropropane, amyl chloride, dichloropentane, monochlorobenzene, o-dichlorobenzen, trichlorobenzene, and bromobenzene; alcoholic and phenolic solvent such as methanol, ethanol, n-propylalcohol, isopropylalcohol, n-butylalcohol, isoamylalcohol, synthetic amylalcohol, fusel oil, methylisobutylcarbinol, n-hexylalcohol, 2-ethylbutanol, n-octylalcohol, 2-ethylhexanol, cyclohexanol, furfurylalcohol, tetrahydrofurfurylalcohol, benzylalcohol, phenol, and cresol; ether solvent such as ethylether, isopropylether, n-butylether, dichloroethylether, anisole, dioxane, tetrahydrofuran, tetrahydropyran, and benzylethylether; acids and their esters such as formic acid, acetic acid, acetic anhydride, butyric acid, methyl formate, ethyl formate, butyl formate, amyl formate, methyl acetate, ethyl acetate, isopropyl acetate, butyl acetate, S-butyl acetate, amyl acetate, isoamyl acetate, 2-ethyihexyl acetate, cyclohexyl acetate, ethyl propionate, butyl propionate, amyl propionate, butyl butyrate, diethyl carbonate, diethyl oxalate, methyl lactate, ethyl lactate, triethylphosphate, γ-butyrolactone, and trifluoroacetic acid; a polyalcohol, its ethers and esters such as ethylene glycol, ethylene glycol monomethyl ether, ethylene glycol monoethyl ether, ethylene glycol monobutyl ether, ethylene glycol monoacetate, ethylene glycol monomethyl ether acetate, ethylene glycol monoethyl ether acetate, ethylene glycol dimethyl ether, diethylene glycol, diethylene glycol monomethyl ether, diethylene glycol monoethyl ether, diethylene glycol dimethyl ether, triethylene glycol, propylene glycol, hexylene glycol, and glycerin; aldehyde, acetal, and ketone such as furfural, methylal, acetal, acetone, methylethylketone, methylisobutylketone, diisobutylketone, methyl oxide, acetylacetone, diacetonealcohol, cyclohexanone, methylcyclohexanone, and isophorone; a nitrogen compound such as nitromethane, nitroethane, 1-nitro-propane, 2-nitro-propane, nitrobenzene, acetonitrile, diethylamine, triethylamine, cyclohexylamine, ethylene diamine, aniline, pyridine, picoline, quinoline, monoethanolamine, diethanolamine, morpholime, dimethyl formamide, dimethylacetoamide, hexamethyl phospholtriamide, and N-methyl pyrrolidone; a sulfuric compound such as anhydrous sulfide, carbon disulfide, thiophene, sulfolane, and dimethylsulf oxide; can be used as a solvent in the present invention. Among those, it is preferable to use a solvent, which can solubilize either cyclotetrasaccharide or a derivative of cyclotetrasaccharide of the present invention, to increase the efficiency of the synthesis. In the case of being preferable to react under anhydrous condition, it is desirable to remove moisture by a suitable dehydrating agent. In the case of being acceptable to contain water in the reaction system, water can be used as a solvent. Those solvents can be used alone or along with one or more other solvents by mixing.

Cyclotetrasaccharide usable in the present invention is not restricted to its origin and a process for producing it as long as not affecting the object of the present invention. Cyclotetrasaccharide, which is conventionally obtainable by allowing alternanase to act on alternan, and one which is obtainable by the method disclosed in International Publication No. WO 02/10,361 (international application No. PCT/JP01/06,412), i.e., an enzymatic method of allowing α-isomaltosyl-transferring enzyme and α-isomaltosylglucosaccharide-forming enzyme to act on starch, can be used. In the case of producing a derivative of cyclotetrasaccharide in an industrial level, the later method described above is advantageously used because cyclotetrasaccharide can be obtained in lower cost. Varying depending on the kind of objective derivative and the reaction system, a desirable concentration of cyclotetrasaccharide in a solvent can be selected from the range of, usually, 0.1-80% (w/v), desirably, 0.1-20% (w/v).

α-Isomaltosyl-transferring enzymes, disclosed in International Publication No. WO 01/90,338 (international application No. PCT/JP01/04,276), and α-isomaltosylglucosaccharide-forming enzymes, disclosed in International Publication No. WO 02/10,361 (international application No. PCT/JP01/06,412), can be used for producing cyclotetrasaccharide from starch in an industrial scale. Both above enzymes can be prepared by cultivating Bacillus globisporus C9 (FERM BP-7143), Bacillus globisporus C11 (FERM BP-7144), Bacillus globisporus N75 (FERM BP-7591), Arthrobacter globiformis A19 (FERM BP-7590), or Arthrobacter ramosus S1 (FERM BP-7592) according to the method described in above specifications. Both above enzymes prepared from above strains have physicochemical properties shown in Table 1. Cyclotetrasaccharide can be produced from starch material with a satisfactory yield by using above enzymes in combination. The cyclotetrasaccharide content of the preparation, obtained by the method described in above specifications, is usually about 60% (w/w) (hereinafter, "% (w/w)" is briefly abbreviated as "%", unless specified otherwise) or higher, and the saccharide can be used for producing the derivative of cyclotetrasaccharide of the present invention. In the case of desiring a preparation having a relatively high cyclotetrasaccharide content, high cyclotetrasaccharide content fractions can be collected by applying the low cyclotetrasaccharide content preparation to a strong-acid cation exchange resin (salt form) column chromatography with fixed-bed, moving bed, or semi-moving bed. The high cyclotetrasaccharide content fractions, thus obtained, contain cyclotetrasaccharide in a content of about 98%, on a dry solid basis, and can be used as materials for producing a derivative of cyclotetrasaccharide of the present invention.

TABLE 1

|  | α-Isomaltosyl-transferring enzyme | α-Isomaltosyl-glucosaccharide-forming enzyme |
| --- | --- | --- |
| Molecular weight (Analytical method) | About 82,000-136,000 daltons (SDS-gel electrophoresis) | About 74,000-160,000 daltons (SDS-gel electrophoresis) |
| Isoelectric point (pI) (Analytical method) | about 3.7-8.3 Ampholine electrophoresis | about 3.8-7.8 Ampholine electrophoresis |
| Optimum temperature | about 45-50° C. | about 45-60° C. or about 45-65° C. (in the presence of 1 mM $Ca^{2+}$) |
| (Condition) | Reaction at pH 6.0 for 30 min | Reaction at pH 6 or pH 8.4 for 60 min |
| Optimum pH | pH about 5.5-6.5 | pH about 6-8.4 |
| (Condition) | Reaction at 35° C. for 30 min | Reaction at 35° C. for 60 min |
| Thermal stability | Stable up to about 45° C. | Stable up to about 55° C. or about 60° C. (in the presence of 1 mM $Ca^{2+}$) |
| (Condition) | Incubation at pH 6.0 for 60 min | Incubation at pH 6 or pH 8 for 60 min |
| pH Stability | Stable in a range of pH about 3.6-10.0 | Stable in a range of pH about 4.5-10.0 |
| (Condition) | Incubation at 4° C. for 24 hours | Incubation at 4° C. for 24 hours |

In the case of selecting the reaction system not preferring moisture as a process for producing the derivative of cyclotetrasaccharide in the present invention, it is preferable to use a preparation of cyclotetrasaccharide, comprising moisture as low as possible, for increasing the reaction yield. Therefore, cyclotetrasaccharide in a solid or powdery form, having low moisture content, produced by suitable concentrating and drying process, is used in such a case. Since crystalline cyclotetrasaccharide may have five to six molecules of water per molecule even in a solid or powdery form, it is desirable to use anhydrous crystalline and anhydrous amorphous cyclotetrasaccharide, which are disclosed in International Publication Nos. WO 01/90,338 (international application No. PCT/JP01/04,276) and WO 02/10,361 (international application No. PCT/JP01/06,412) and Japanese Patent Application No. 10,991/2001, for producing the derivative of cyclotetrasaccharide of the present invention. Preferable moisture content of cyclotetrasaccharide is 3% or lower, more preferably, 1% or lower.

When material cyclotetrasaccharide can not be dissolved sufficiently because of using a solvent which can hardly or not dissolve the saccharide, it is desirable to use powdery cyclotetrasaccharide for increasing the reaction efficiency. The diameter of granule of powdery cyclotetrasaccharide should be controlled to a suitable size to the solvent and the reaction condition. Usually, granule having the smaller diameter gives the faster reaction rate. Therefore, the reaction rate can be controlled by choosing the diameter of the granule. The diameter of powdery cyclotetrasaccharide, used in the present invention, can be arbitrarily determined according to the objective derivative or reaction system, and is controlled to be, usually, 500 μm or lower, preferably, 0.1-250 μm, more preferably, 1-100 μm.

Lewis acids such as aluminum chloride, aluminum bromide, zinc chloride, antimony chloride, boron fluoride, copper chloride, tin chloride, and phosphorus chloride; Brønsted acids such as hydrogen fluoride and phosphoric acid; hydroxide or oxide of alkaline metal or alkaline earth metal such as sodium hydroxide, potassium hydroxide, magnesium hydroxide, calcium hydroxide, magnesium oxide, and potassium oxide; bases such as basic organic compounds including amines; and heavy metals such as platinum, palladium, nickel, cobalt, copper, chromium, molybdenium, silver, zinc and their oxide, sulfide, and Raney catalyst can be used as catalysts in the present invention, and one or more catalysts can be used in combination. These catalysts can be optionally selected in accordance with the objective derivative of cyclotetrasaccharide and the reaction system. The amount of catalyst is preferable to be, usually, 0.0001% or higher, desirably, 0.001-10,000%, more desirably, 0.01-1,000% to the weight of cyclotetrasaccharide.

The reactive reagent as referred to as in the present invention means one or more reagents selected from the group consisting of acids, bases, alcohols, aldehydes, ketones, halogens, amines, cyanogens, nitrites, oxiranes, isocyanates, isothiocyanates, thiols, sulfones and their reactive derivatives, introducing hydrocarbon group, substituents having oxygen, those having nitrogen, those having sulfur, and those having halogen into cyclotetrasaccharide. The molar ratio of the reactive reagent to cyclotetrasaccharide can be suitably determined in accordance with the objective derivative of cyclotetrasaccharide and the reaction system, and selected from the range of, usually, 0.01-10,000 mole %, desirably, 0.1-1,000 mole %.

Reaction conditions such as reaction temperature, reaction time, and reaction pressure can be suitably selected in accordance with the objective derivative of cyclotetrasaccharide and the reaction system. Generally, it is preferable to set reaction temperature to a relatively high one in the case of endothermic reaction and a relatively low one in the case of exothermic reaction. The reaction temperature can be usually selected from the range of that proceeding the reaction substantially, desirably, −50 to 200° C. The reaction time can be usually selected from the range of that until accomplishing the reaction, desirably, one minute to 100 hours. The reaction can be carried out, usually, under normal pressure, and, optionally, under pressurized or reduced pressure condition. Optionally, the reaction can be accelerated by irradiating the reaction mixture with lights such as ultraviolet rays, visible rays, and infrared rays; radiations such as X-rays and γ-rays; and electromagnetic radiation.

A reaction product comprising the derivative of cyclotetrasaccharide of the present invention, thus obtained, can be usually used intact after removing remaining reactive reagents and/or solvent by the methods such as filtration, extraction, separating, separatory precipitation, dialysis, and distillation. In the case of requiring the derivative of cyclotetrasaccharide, having a relatively high purity, the reaction product can be purified by conventional methods for purifying saccharides or saccharide derivatives such as thin-layer chromatography, column chromatography, ion-exchange chromatography, high performance liquid chromatography, distillation, and crystallization. Those purification methods can be optionally and arbitrarily used in combination.

A reaction system using a solvent can be usually selected for producing the derivatives of the present invention industrially. In some cases, other reaction system can be used as in the case of cyclodextrins. For example, co-precipitation method, slurry method, paste method, and dry-mixing method, described in Allan R. Hedges, *Chemical Reviews*, Vol. 98, 1998, can be used.

The followings explain representative processes for producing the derivatives of cyclotetrasaccharide of the present invention.

<1> Esterification and etherification

Esterification and etherification can be used for introducing hydrophobic groups such as alkyl group and aromatic hydrocarbon group into cyclotetrasaccharide. Esters constructed by cyclotetrasaccharide and a carbonic acid such as acetic acid and benzoic acid can be obtained by reacting cyclotetrasaccharide with corresponding acid anhydrides or acid halides in a basic solvent such as pyridine. Esters constructed by cyclotetrasaccharide and sulfuric acid can be obtained by reacting cyclotetrasaccharide with a complex of sulfur trioxide and dimethyl sulfoxide or pyridine in a flow current of inert gas or rare gas. Esters constructed by cyclotetrasaccharide and fatty acids such as caproic acid, caprylic acid, capric acid, lauric acid, myristic acid, palmitic acid, stearic acid, arachic acid, behenic acid, lignoceric acid, zoomaric acid, oleic acid, linoleic acid, linolenic acid, gadoleic acid, erucic acid, and selacoleic acid can be obtained by condensing cyclotetrasaccharide with those fatty acids in the presence of a basic catalyst or reacting cyclotetrasaccharide with corresponding fatty acid halides.

<2> Sulfonylation

Sulfonylated derivatives of cyclotetrasaccharide are useful as reaction intermediates for synthesizing various derivatives. After introducing tosyl (4-methylbenzenesulfonyl) group, mesyl (methanesulfonyl) group, or other related allylsulfonyl groups into cyclotetrasaccharide, substituents such as amino group, azido group, halogen group can be introduced into the resulting derivatives by nucleophilic displacement reaction. The position which should be introduced substituent can be restricted by selecting the reaction condition. For example, tosylated cyclotetrasaccharide, cycrotetrasaccharide whose primary hydroxyl groups are tosylated, can be obtained by reacting cyclotetrasaccharide with tosyl chloride in pyridine. Ferrocenecarbonyl cyclotetrasaccharide can be produced by introducing ferrocenecarbonyl group into cyclotetrasaccharide by allowing the saccharide to react with sodium ferrocenecarbonate in dimethylsulfoxide and heating. The reaction can be carried out according to the method described in Akihiko Ueno et al., *Macromolecular Chemistry, Rapid Communications*, Vol. 6, pp. 231-233, 1985, and Iwao Suzuki et al., *Bulletin of the Chemical Society of Japan*, Vol. 66, pp. 1472-1481, 1993. Amino cyclotetrasaccharide can be produced by the steps of diazotizing above tosyl-cyclotetrasaccharide with sodium azide and reducing the resulting derivative to convert the diazo group into amino group (J. Boger et al., *Helvetica Chimica Acta*, Vol. 61, pp. 2190, 1978). On the other hand, secondary hydroxyl groups of cyclotetrasaccharide are tosylated by reacting cyclotetrasaccharide with m-nitrophenyltosylate at 60° C. in dimethylformamide-alkaline aqueous solution (Akihiko Ueno et al., *Tetrahedron Letters*, Vol. 23, pp. 3451, 1982). S-Alkyl derivative of cyclotetrasaccharide can be produced by the steps of epoxidizing tosyl-cyclotetrasacchride under an alkaline condition and reacting the resultant with alkyl sulfide to introduce alkyl group via sulfide bond into cyclotetrasaccharide (R. Breslow et al., *Journal of the American Chemical Society*, Vol. 105, pp. 1390, 1983; Murakami et al., *Chemistry Letter*, pp. 553, 1988; and Ikeda et al., *Tetrahedron Letters*, Vol. 31, pp. 5045, 1990).

<3> 2,2,6,6-Tetramethyl-1-piperidinyloxilation

This process can be used for producing carboxylated cyclotetrasaccharide. Carboxylated cyclotetrasaccharide can be obtained by oxidizing primary hydroxyl groups of cyclotetrasaccharide to form carboxyl group by the steps of mixing cyclotetrasaccharide with 2,2,6,6,-tetramethyl-1-pipetidinyloxi-sodium perchlorate, sodium bromide, and sodium chlorite and reacting at pH 9-11. Carboxyl group can be bound with compounds having amino group via amide bond. The reaction can be carried out according to the method described in Ichikawa et al., *Tetrahedron: Asymmetry*, Vol. 11, pp. 389-392, 2000.

<4> Polymerization

This process can be used for polymerizing cyclotetrasaccharides. Polymerized cyclotetrasaccharide in a gel form can be obtained by reacting cyclotetrasaccharide with epichlorohydrin in alkaline solution for cross-linking. The reaction can be carried out according to the methods described in Jozsef Szejtli et al., *Journal of Materials Chemistry*, Vol. 7, No. 4, 1997; Akira Hamada, *Modular Chemistry*, edited by J. Michl, pp. 361-370, 1997; and Komiyama, "Kagaku (Science)" (in Japanese), Vol. 59, No. 2, pp. 105-112, 1989.

<5> Introduction of various functional groups

Hydroxyl groups of cyclotetrasaccharide can be substituted with other functional groups. Derivatives of cyclotetrasaccharide, having a reactive functional group, can be bound with other organic compounds. An aldehyde group(s) can be introduced into cyclotetrasaccharide, for example, by the steps of introducing methyl halide group into cyclotetrasaccharide and oxidizing the resultant with dimethylsulfoxide or hexamine. A halogen group(s) can be introduced into cyclotetrasaccharide: for example, a chloro-group(s) can be introduced into cyclotetrasaccharide by the steps of mixing the saccharide with concentrated hydrochloric acid and zinc chloride and heating or allowing them to react in a flow current of dried hydrochloric acid gas. An amino group(s) can be introduced into cyclotetrasaccharide by the steps of allowing the saccharide to react with halogenocarboxylic acid halide or epichlorohydrin to produce cyclotetrasaccharide halide and allowing the resultant to react with ammonia. A mercapto-group(s) can be introduced into cyclotetrasaccharide by the steps of allowing the above cyclotetrasaccharide halide to react with sulfurating agent such as sodium thiosulfate and reducing the resultant with lithium aluminum hydride.

The derivatives of cyclotetrasaccharide of the present invention can be bound with other substances via their functional groups. Therefore, they can be bound with biologically and physiologically active substances: for example, cytokines such as interferon, tumor necrosis factor, erythropoietin, and interleukin 2; hormones such as insulin and steroid; and amino acids, oligopeptides, polypeptides, proteins, nucleic acids, saccharides, lipids, vitamins, and antibiotics. Also, since they can be bound with coloring materials and fluorescent substances such as dansylgycine, N,N'-dimethylaminobenzoyl group, methyl red, paramethyl red, anthracene-9-carbonyl group, pyrene, and azobenzene, they can be used as reagents for the detection. Furthermore, since they can be bound with 2-hydroxypropyl group, pyridoxamine group, p-methoxyphenol, p-nitrophenol, benzofuroxan, and metaphorbol, they can be used as reaction catalysts for other substances. Also, since they can be bound with high molecular carrier such as polyvinylalcohol, polyacrylamide, polyethyleneglycol, polypropyleneglycol, polymethylvinylether, cellulose, and their derivatives, they can be used for analyzing or purifying other substances.

Cyclotetrasaccharide provides twelve non-anomeric hydroxyl groups as reactive functional groups for usual substituting reactions. This means that a composition containing derivatives of cyclotetrasaccharide, which have different degree of substitution, in various proportions would be formed depending on the kinds and the conditions of the reaction. The degree of substitution can be controlled by controlling time, temperature, and reagent concentration of the reaction. For avoiding the substitution by later reaction, adequate protection groups can be introduced in advance into cyclotetrasaccharide. The degree of substitution can be conventionally determined by measuring the integral values of $^1$H-NMR or by spectroscopic procedures. The derivatives of cyclotetrasaccharide of the present invention are not restricted by their degrees of substitution. The derivatives various degree of substitution can be used according to their uses. Usually, derivatives having an average degree of substitution of one or more can be preferably used. Since cyclotetrasaccharide has two primary hydroxyl groups and ten secondary hydroxyl groups, substituents can be selectively introduced by using their subtle difference of reactivities.

The derivatives of cyclotetrasaccharide, which are obtained by the process of the present invention, can be widely used in various fields such as catalyst, fiber, wrapping, construction, paint, analysis, electrical engineering, and correspondence as well as food industry, cosmetic industry, and pharmaceutical industry. The derivatives of cyclotetrasaccharide of the present invention, into which are introduced hydrophobic groups such as phenyl group, alkyl group, and acetyl group; are lipophilic and useful as surfactants for foods, cosmetics, and pharmaceuticals. The derivatives into which are introduced sulfate ester, can be advantageously incorporated into cosmetics as a good moisture-retaining agent or skin care agent. The derivatives into which are introduced functional groups having a binding ability such as vinyl group, amino group, carboxyl group, mercapto group, and halogen group, or substituents having those functional groups, can be bound with other organic compounds and/or cyclotetrasaccharide. Therefore, they can be used for producing novel organic compounds by forming polymers as well as homo- and heterodimers; producing supports for analysis, detection, and purification by binding with macromolecular supports; changing properties of other compounds as well as proteins; and reacting with other compounds in the presence of catalysts. The derivatives, introduced functional groups such as cyano group, nitro group, and nitroso group or substituents having those functional groups, can be used to pharmaceuticals as antibacterial agent, immunity activating agent, and anticancer agent; and to materials for fibers, wrappings, and constructions. Since the derivatives of cyclotetrasaccharide of the present invention, having a dissociative functional group such as carboxyl group, halogen group, etc., and they having a polarizing functional group such as hydroxyl group, amino group, etc., have a dielectric property; they can be used as additives for fuel battery. The derivatives of cyclotetrasaccharide of the present invention, having an alkyl alcohol group such as hydroxymethyl group, hydroxyethyl group, hydroxypropyl group, etc., show a higher solubility in water than that of cyclotetrasaccharide. The derivatives of cyclotetrasaccharide of the present invention, having two or more functional groups and/or two or more kinds of functional groups, can be used as a cross-linking agent.

Since the derivatives of cyclotetrasaccharide of the present invention have a structure of cyclotetrasaccharide as a basic frame, they usually have the properties and functions of cyclotetrasaccharide partially. Therefore, they can be used for the similar object with cyclotetrasaccharide. They can be used according to the uses of cyclotetrasaccharide, which are disclosed in International Publication Nos. WO 01/90,338 (international application No. PCT/JP01/04,276) and WO 02/10,361 (international application No. PCT/JP01/06,412), applied for by the same applicant as the present invention. The following outlines the uses of the derivatives of cyclotetrasaccharide of the present invention.

The derivatives of cyclotetrasaccharide of the present invention usually have the properties and functions of cyclotetrasaccharide partially though they are varied depending on the substituents. In many cases, such derivatives show a low or non-sweetness and a satisfactory taste, and are non-reducing and stable saccharides. Therefore, when they are admixed with other materials, especially, amino acids and substances constructed by amino acids such as oligopeptides and proteins, and processed, the mixture would not turn brownish and not form strange smells, and other materials mixed would not be damaged. Therefore, the derivatives of cyclotetrasaccharide of the present invention can be used as materials in various fields such as foods, cosmetics, and pharmaceuticals.

Since the derivatives of cyclotetrasaccharide of the present invention are constructed with cyclotetrasaccharide as a basic frame, they are substantially hardly hydrolyzed by amylases and α-glucosidases. When they are orally ingested, they are not assimilated and hardly fermented by intestinal bacteria. Therefore, they can be used as water-soluble dietary fibers having an extremely low calorie. Also, since the derivatives of cyclotetrasaccharide of the present invention are hardly fermented by dental caries-inducing bacteria, they can be used as sweeteners hardly inducing dental caries. Further, they also have a function of preventing the adhesion and solidifying of solids in oral. The derivatives of cyclotetrasaccharide of the present invention exhibit various properties such as osmosis-controlling ability, filling ability, gloss-imparting ability, moisture-retaining ability, viscosity, ability of preventing the crystallization of other saccharides, and less fermentability. The derivatives of cyclotetrasaccharide of the present invention may be harmful and poisonous depending on the kind of substituents. If the derivatives of cyclotetrasaccharide of the present invention and the compositions comprising the same are confirmed to be safe, they can be advantageously used to various compositions such as foods, tobacco, cigarette, feeds, pet foods, cosmetics, and pharmaceuticals as seasoning, taste-improving agent, quality-improving agent, stabilizer, discoloration-preventing agent or filler.

The derivatives of cyclotetrasaccharide of the present invention and the compositions comprising the same can be incorporated into foods, cosmetics, and pharmaceuticals along with other ingredients which are usually used for foods, cosmetics, and pharmaceuticals. The following shows the other ingredients concretely.

The derivatives of cyclotetrasaccharide of the present invention and the compositions comprising the same can be admixed with various fats: for example, vegetable oil such as avocado oil, almond oil, olive oil, sesame oil, safflower oil, soybean oil, camellia oil, apricot kernel oil, castor oil, and cotton seed oil; plant fats such as cacao butter, coconut butter, palm oil, and Japan wax; and animal oils such as minke oil, egg yolk oil, and turtle oil.

The derivatives of cyclotetrasaccharide of the present invention and the compositions comprising the same can be admixed with various waxes: for example, plant waxes such as jojoba oil, carnaba wax, and candelila wax; animal-origin wax such as sperm whale oil, Baird's beaked whale oil, beeswax, whale wax and lanolin; and mineral waxes such as montan wax.

The derivatives of cyclotetrasaccharide of the present invention and the compositions comprising the same can be admixed with various hydrocarbons: for example, mineral hydrocarbons such as paraffin (alias "solid paraffin"), liquid paraffin, ceresin, microcryatalline wax, and vaseline; and hydrocarbons of animal origin such as squalane and squalene.

The derivatives of cyclotetrasaccharide of the present invention and the compositions comprising the same can be admixed with various fatty acids: for example, lauric acid, myristic acid, palmitic acid, stearic acid, oleic acid, behenic acid, undecylic acid, lanolin fatty acid, hard lanolin fatty acid, soft lanolin fatty acid, isostearic acid, and those derivatives.

The derivatives of cyclotetrasaccharide of the present invention and the compositions comprising the same can be admixed with various alcohols: for example, higher alcohols (including polyhydric alcohols) such as lauryl alcohol, cethanol, cetostearyl alcohol, stearyl alcohol, oreyl alcohol, behenyl alcohol, lanoline alcohol, hydrogenated lanoline alcohol, hexyldecanol, octyldodecanol, and polyethyleneglycol; lower alcohols (including polyhydric alcohols) such as ethanol, propanol, isopropanol, butanol, ethyleneglycol, propyleneglycol, and glycerin; and their derivatives.

The derivatives of cyclotetrasaccharide of the present invention and the compositions comprising the same can be admixed with various alcohols: for example, higher alcohols (including polyhydric alcohols) such as lauryl alcohol, cethanol, cholesteryl alcohol, stearyl alcohol, oreyl alcohol, behenyl alcohol, lanoline alcohol, hydrogenated lanolin alcohol, hexyldecanol, octyldodecanol, and polyethyleneglycol; lower alcohols (including polyhydric alcohols) such as ethanol, propanol, isopropanol, butanol, ethyleneglycol, propyleneglycol, and glycerin; and their derivatives.

The derivatives of cyclotetrasaccharide of the present invention and the compositions comprising the same can be admixed with various surfactants: for example, anionic surfactants such as zinc laurate, zinc myristiate, zinc palmitate, magnesium stearate, sodium laurylsulfate, triethanolamine laurylsulfate, sodium cetlysulfate, sodium polyoxyethylenelaurylether sulfate, triethanolamine polyoxyethylenelaurylether sulfate, polyoxyethylenecetylether phosphate, polyoxyehylenealkylphenylether phosphate, sodium lauroylsarcosine, coconut oil fatty acid sarcosinetriethanolamine, sodium methyltaurine-coconut oil fatty acid, and soybean phospholipid; cationic surfactants such as stearyltrimethylammonium chloride, distearyldimethylammonium chloride, benzalkonium chloride, cetylpyridinium chloride, alkylisoquinrinium bromide, and dodecyldimethyl-2 -phenoxyethylammonium bromide; amphoteric surfactants such as sodium β-laurylaminopropionate, betaine lauryldimethylaminoacetate, and betaine 2-alkyl-N-carboxymethyl-N- hydroxyethylimidazorium; non-ionic surfactants such as self-emulsifying glycerin monostearate, lipophilic glycerin monostearate, propyleneglycol dioreate, sorbitan monolauryate, sorbitan monooreate, sucrose-fatty acid ester, monoethanolamide undecylenate, diethanolamide-coconut oil fatty acid ester, polyethyleneglycol monooreate, myristyl lactate, polyoxyethylene-cetyl ether, polyoxyethylene-octylphenyl ether, polyoxyethylenesorbit monolaurate, polyoxyethylenesorbitan monolaurate, polyoxyethylenesorbitan monostearate, polyoxyethylenesorbitan trioreate, polyoxyethylenesorbitan tetraoreate, polyoxyethlene-castor oil and polyoxyethylene-hardening castor oil; and their derivatives.

The derivatives of cyclotetrasaccharide of the present invention and the compositions comprising the same can be admixed with various coloring materials: for example, red-tar-colorings such as Amaranth, Erythrosine, Rose bengale, Acid red, Lake red C, Lithol red, Rhodamine, Brilliant Lake red, Eosin YS, Violamine R, Brilliant Fast scarlet, and Ponceau R; orange-tar-colorings such as Dibromofluoresceine, Permanent orange, Erythrosine yellow NA, and Orange I; yellow-tar-colorings such as Tartrazine, Sunset yellow, Uranine, Bentizine yellow G, Naphthol yellow S, and Yellow AB; green-tar-colorings such as Fast green FCF, Alizarin Cyanine green F, Light Green SF yellow, and Naphthol green B; blue-tar-colorings such as Brilliant blue FCF, Indigocarmine, Indigo, Patent blue NA, Carbanthrene blue, and Sudan blue; brown-tar-colorings such as Resorcin brown; purple-tar-colorings such as Alizurin purple and Alizurol purple; black-tar-colorings such as Naphthol blue black; inorganic colorings such as zinc oxide, titanium oxide, cobalt hydroxide, aluminium hydroxide, talc, kaolin, mica, bentonite, manganese violet, and mica titanium; carotenoide-colorings such as β-carotene, lycopene, and crocin; flavonoide-colorings such as sisonine, safflower yellow, rutin, quercetin, and hesperidin; flavin-colorings such as riboflavin; quinone-colorlings such as cochineal, alizarin and shikonin; and their derivatives.

The derivatives of cyclotetrasaccharide of the present invention and the compositions comprising the same can be admixed with various fragrant materials: for example, animal fragrant such as musk, civet, castoreum, and ambergris; plant fragrant such as distilled materials (essential oils) obtainable by steam distillation from fruit of anis, leaf of basil, fruit of caraway, cortex of cinnamon, seed of coriander, flower of lavender, seed of nutmeg, leaf of peppermint, flower of rose, seed or leaf of rosemary, and leaf of thymu; extracts (generally classified into absolutes, resinoids, oleoresins, and tinctures) obtainable from flower of hyacinth, flower of jasmine, flower of minosa, flower of rose, and seed of vanilla; synthetic fragrances such as acetophenone, anethole, benzylalcohol, butytlacetate, camphor, citral, citronellal, cuminaldehyde, estragole, ethylvanillin, geranylacetate, linalol, menthol, methyl-p-crezol, methyl salisylate, phenylacetic acid, and vanilline; and their derivatives. Further, prepared fragrances produced by suitably mixing those fragrances can be used in the present invention.

The derivatives of cyclotetrasaccharide of the present invention and the compositions comprising the same can be admixed with various hormones: for example, ovarian follicle hormones such as estrone and estradiol; corpus luteum hormones such as progesterone and pregnenolone; adrenal cortex hormones such as cortisone, hydrocortisone, prednisone, and prednisolone; and various vitamins: for example, compounds belonging vitamin A such as retinol, retinoic acid, α-, β-, and γ-carotene, and their derivatives; compounds belonging to vitamin B such as thiamine (vitamin $B_1$), riboflavin (vitamin $B_2$), pyridoxine, pyridoxal, pyridoxamine (hereinbefore, vitamin $B_6$), and their derivatives; compounds belonging to vitamin C such as L-ascorbic acid, glycosyl-L-ascorbic acids such as 2-O-α-D-glucosyl-L-ascorbic acid, acyl-derivatives of L-ascorbic acid and glycosyl-L-ascorbic acids (alias "lipophilic vitamin C"), other L-ascorbic acid derivatives such as L-ascorbic acid sulfate (sulfuric acid ester); compounds belonging to vitamin D such as ergocalciferol, cholecalciferol and their derivatives; and compounds belonging to vitamin E such as α-, β-, γ-, and δ-tocopherol, α-, β-, γ-, and δ-tocotrienol, and their derivatives.

In addition to the aforesaid plant extracts used as flavors, the derivatives of cyclotetrasaccharide of the present invention and the compositions comprising the same can be admixed with various plant extracts: for example, mayweed extract, sage extract, aloe extract, salvia extract, *Angelica keiskei* extract, avocado extract, nettle extract, fennel extract, oolong tea extract, cork tree bark extract, barley extract, gumbo extract, orris extract, seaweed extract, Chinese quince extract, *Glycyrrhiza glaba* extract, quince seed extract, gardenia extract, "kumazasa" extract, cinnamon extract, rice bran extract, fermented rice bran extract, stevia extract, celery extract, sialid extract, soybean extract, thymu extract, tea extract, camellia extract, *Ligusticum acutilobum* extract, corn extract, carrot extract, rugosa rose extract, cypress extract, loof ah extract, safflower extract, pine extract, peach extract, eucalyptus tree extract, strawberry geranium extract, Chinese lemon extract, lily extract, adlay extract, tansy extract, *Cyanobacteria* extract, seaweed extract, apple extract, *Memordica charantia* extract, and lettuce extract; and compounds isolated from plants such as hinokitiol, azulene, chlorophyll, and glycyrrhizin. A placenta extract can be used in the present invention as an animal extract.

The derivatives of cyclotetrasaccharide of the present invention and the compositions comprising the same can be admixed with microbial extracts such as yeast extract. In addition to salts which are generally accepted and usually used, the derivatives of cyclotetrasaccharide of the present invention and the compositions comprising the same can be advantageously admixed with natural salts (including solutions) such as sea water, bittern, marine deep water, dried sea water, and mineral salts.

The derivatives of cyclotetrasaccharide of the present invention and the compositions comprising the same can be admixed with various ultraviolet-ray absorbing agent: for example, ethyl paraaminobenzoate, ethyl paraaminobenzoate hexyl ester, cinoxate, ethyl paradimethyl cinnamate hexyl ester, 2-(2-hydroxy-5-methylphenyl)-benzotriazole, oxybenzozone, urocanynic acid, ethyl urocanyate, ruin, and quercetin; their derivatives; and organic compounds having an ultraviolet-ray shielding activity such as 5-chlorouracil, guanine, and cytosine; and photosensitive dye: for example, 2,2'[3'-[2-(3-heptyl-4-methyl-2-thiazoline-2-yliden) ethylidene]propenylene]-bis-[3-heptyl-4-methyl]thiazoliniumiodide (alias "PLATONIN"), 2-[2-(3-heptyl-4-methyl-2-thiazoline-2-ylidene) methyne]-3-heptyl-4-methylthiazoliniumiodide (alias "PIONIN"), 6-[2-[(5-bromo-2-pyridyl)amino]vinyl]-1-ethyl-picoliniumiodide (alias "TAKANAL"), and 2-(2-anilinovinyl)-3,4-dimethyloxazoliniumiodide (alias "LUMINEX"); and their derivatives.

In addition to the aforesaid ingredients having an antioxidative effect, the derivatives of cyclotetrasaccharide of the present invention and the compositions comprising the same can be admixed with various anti-oxidizing agents: for example, propyl gallate, butyl gallate, actyl gallate, dodecyl gallate, nordihydrogaialenic acid (alias "NDGA"), butylhydroxyanisole (alias "BHA"), dibutylhydroxytoluene (alias "BHT"), 4-hydroxymethyl 1-2,6-ditertiarybutylphenol, catechin, rutin, and quercetin; and their derivatives.

In addition to the aforesaid ingredients having a preserving and sterilizing effect, the derivatives of cyclotetrasaccharide of the present invention and the compositions comprising the same can be admixed with various preservatives and disinfectants: for example, phenolic compounds such as phenol, parachloromethacresol, resorcin, paraoxybenzoic acid ester, and cresol; acids (including their salts) such as benzoic acid, sorbic acid, salicylic acid, and boric acid; halogenized bisphenolic compounds such as hexachlorophen, bithionol, and dichlorophen; amides such as 3,4,4'-trichlorocarbanilide and undecylenic acid monoethanolamide; quaternal ammonium compounds such as benzalconium chloride, benzetonium chloride, and decalinium chloride; compounds and their derivatives such as chlorohexidine hydrochloric acid, 1-hydroxypyridine-2-thion, and lysozyme hydrochloric acid.

The derivatives of cyclotetrasaccharide of the present invention and the compositions comprising the same can be admixed with antiperspirants and deodorants such as aluminum chloride, zinc chloride, chlorohydroxyl aluminum, allantoin chlorohydroxyl aluminum, and aluminum chlorohydrate; refrigerants such as menthol, spearmint oil, peppermint oil, camphor, thymol, spilanthol, and methylsalicylirate; and chelating agents such as derivatives of ethylendiaminetetraacetate, tripolyphosphoric acid, hexamethacrylic acid, dihydroethylglycine, citric acid, tartaric acid, gluconic acid and sugar acid.

In addition to the aforesaid ingredients having an skin-whitening effect, the derivatives of cyclotetrasaccharide of the present invention and the compositions comprising the same can be admixed with various skin-whitening agents; for example, nucleic acid such as anti-sense oligonucleotides (for example, an anti-sense oligonucleotide against tyrosinase gene); compounds such as kojic acid, lactic acid, anthranilic acid, coumarin, benzotriazole, imidazoline, pyrimidine, dioxane, furan, pyrone, nicotinic acid, albutin, baicalin, bicalen, and berberine; and their derivatives; inhibitor for melanine-formation, inhibitor for tyrosinase-formation, inhibitor of tyrosinase.

In addition to the aforesaid ingredients having an anti-inflammatory effect, the derivatives of cyclotetrasaccharide of the present invention and the compositions comprising the same can be admixed with various anti-inflammatory agents; for example, allantoin, allantoin acetyl-D,L-methionine, allantoin β-glycyrrhetinoate, ichthammol, indomethacin, acetylsalicylic acid, diphenhydramine chloride, guaiazulene, chamazulene, chiorpheniramine maleate, glycyrrhzinoic acid, glycyrrhetinoic acid, and oriental gromurell extract; and enzymes such as protease, lipase, and lysozyme, which originate from microorganisms such as *Bacillus, Actinomycetes*, and yeasts; plants; and animals.

The derivatives of cyclotetrasaccharide of the present invention and the compositions comprising the same can be admixed with various saccharides; for example, oligosaccharides such as xylose, arabinose, glucose, fructose, galactose, tagatose, sucrose, maltose, lactose, trehalose, panose, maltotriose, and maltotetraose; cyclic saccharides such as cyclotetrasaccharide, and α-, β-, and γ-cyclodextrin; sugar alcohols such as xylitol, arabitol, sorbitol, maltitol, and mannitol; polysaccharide, their derivatives and partial hydrolyzates such as hyaluronic acid, chondroitin sulfate, pullulan, cellulose, starch, dextran, pectin, carrageenan, locust bean gum, guar gum, corn syrup, gum arabic, tragacanth gum, xanthan gum, glucomannan, and chitin.

The derivatives of cyclotetrasaccharide of the present invention and the compositions comprising the same can be admixed with various amino acids; for example, glycine, serine, threonine, tyrosine, cysteine, cystine, asparagine, glutamine, pyrrolidone carboxylic acid, hydroxyproline, pipecolic acid, sarcosine, homocysteine, homoserine, citrulline, aspartic acid, glutamic acid, cysteine sulfinic acid, algininosuccinic acid, arginine, lysine, histidine, ornithine, alanine, valine, leucine, isoleucine, methionine, phenylalanine, tryptophan, proline, β-alanine, taurine, βamincbutylic aminobutyric acid, and γ-amincbutylic aminobutyric acid; and their salts.

In addition to the aforesaid ingredients having a thickening effect, the derivatives of cyclotetrasaccharide of the present invention and the compositions comprising the same can be admixed with water-soluble polymers; for example, quince seed, sodium alginate, cationated cellulose, hydroxyethylcellulose, carboxymethylcellulose, carboxymethylstarch, propylenglycol alginate, collagen, keratin, casein, albumin, gelatin, hydroxypropyl-trimethylammoniumchloride-ether, polyvinylalcohol, polyvinylpyrrolidone, polyvinylpyrrolidone -vinylacetate copolymerizate, polyethyleneimine, sodium polyacrylate, polyvinylmethylether, and carboxyvinylpolymer; electolyte such as sodium chloride, potassium chloride, and sodium sulfate; and various oils.

While examples of ingredients, which are able to form salts, are not described in the above explanation. However, salts acceptable to the object can be arbitrarily used in the present invention even though they are not described.

The methods for incorporating the aforesaid various ingredients into derivatives of cyclotetrasaccharide or the composition comprising the same are those which can incorporate such ingredients into a product before completion of their processing, and which can be appropriately selected from the following conventional methods; mixing, kneading, dissolving, melting, soaking, penetrating, dispersing, applying, coating, spraying, injecting, crystallizing, and solidifying. It is preferable to incorporate such ingredients in an amount of, usually, 0.1% or higher, desirably, 1% or higher.

Derivatives of cyclotetrasaccharide of the present invention and the compositions comprising the same can be shaped intact or, if necessary, after mixing with fillers, excipients, and binders, into various shapes such as granules, spheres, sticks, plates, cubes, and tablets.

Varying depend on an introduced substituent, derivatives of cyclotetrasaccharide of the present invention and the compositions comprising the same show sweetness in the same or adjusted level with cyclotetrasaccharide, well harmonize with other tastable materials having sour-, salty-, bitter-, astringent-, delicious-, and bitter-taste, and have a high acid- and heat-tolerance. Thus, they can be advantageously used to sweeten, improve tastes and qualities of general foods and beverages. Derivatives of cyclotetrasaccharide or the compositions comprising the same can be advantageously used as a sweetener, taste-improving agent, quality-improving agent for various foods: for example, soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, derivatives of cyclotetrasaccharide and the compositions comprising the same can be advantageously used to sweeten and improve the taste and quality of "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); western confectioneries such as bun, biscuit, cracker, cookie, pie, pudding, butter cream, custard cream, cream puff, waffle, sponge cake, doughnut, chocolate, chewing gum, caramel, nougat, and candy; frozen desserts such as ice cream and sherbet; syrups such as a "kajitsu-no-syrup-zuke" (a preserved fruit) and "korimitsu" (a sugar syrup for shaved ice); pastes such as flour paste, peanut paste, and fruit paste; processed fruits and vegetables such as jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as "takuan-zuke-no-moto" (a premix for pickled radish), and "hakusai-zuke-no-moto" (a premix for fresh white rape pickles); meat products such as ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned swellfish), seasoned fish flour such as of Pacific cod, sea bream, shrimp, etc.; "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as synthetic sake, fermented liquor, sake, fruit liquor, low-malt beer, and beer; soft drinks such as coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, peptide foods, and frozen foods. Derivatives of cyclotetrasaccharide or the compositions comprising the same can be also used for improving preference and physical properties of feeds and pet foods for animals and pets such as domestic animals, poultry, honey bees, silk warms, and fishes. In addition, derivatives of cyclotetrasaccharide or the compositions comprising the same can be advantageously used as preference-improving agent, taste-improving agent, masking agent, quality-improving agent and stabilizer for various compositions such as favorite foods, cosmetics, and pharmaceuticals in a solid, paste, or liquid form such as tobacco, cigarette, tooth paste, lipstick, rouge, lip cream, internal liquid medicine, tablet, troche, cod-liver oil in the form of drop, oral refrigerant, cachou, and gargle. When used as a quality-improving agent or stabilizer, a derivative of cyclotetrasaccharide and the compositions comprising the same can be advantageously incorporated into biologically active substances susceptible to lose their effective ingredients and activities, as well as into health foods and pharmaceuticals containing the biologically active substances. Health foods and pharmaceuticals, having a satisfactory stability and quality, in a liquid, paste, or solid form can be easily produced without losing effective ingredients and activities of biologically active substances: for example, liquid preparations containing lymphokines such as $\alpha$-, $\beta$-, and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor, and interleukin II; liquid preparations containing hormones such as insulin, growth hormone, prolactin, erythropoietin, and follicle-stimulating hormone; liquid preparations containing biological preparations such as BCG vaccine, Japanese encephalitis vaccine, measles vaccine, live polio vaccine, small pox vaccine, tetanus toxin, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamin, riboflavin, L-ascorbic acid, cod liver oil, carotenoide, ergosterol, and tocopherol; highly unsaturated fatty acids or their ester derivatives such as EPA, DHA, and arachidonic acid; liquid preparations containing enzymes such as lipase, esterase, urokinase, protease, $\beta$-amylase, isoamylase, glucanase, and lactase; extracts such as ginseng extract, turtle extract, chlorella extract, aloe extract, and propolis extract; biologically active substances such as royal jelly; living microorganisms pastes of virus, lactic acid bacteria, and yeast.

The following explains a process for producing enzymes which are necessary for producing a material of the present invention, cyclotetrasaccharide.

EXAMPLE A-1

Preparation of Enzymes for Producing Cyclotetrasaccharide: Cultivation of *Bacillus globisporous* C9

$\alpha$-Isomaltosylglucosaccharide-forming enzyme and $\alpha$-isomaltosyl-transferring enzyme, which are used for producing cyclotetrasaccharide using starch as material, were prepared. A liquid culture medium consisting 4% (w/v) of "PINE-DEX #4", a partial starch hydrolyzate commercialized by Matsutani Chemical Industry Co., Ltd., Hyogo, Japan, 1.8% (w/v) of "ASAHIMEAST", a yeast extract commercialized by Asahi Brewery Ltd., Tokyo, Japan, 0.1% (w/v) of dipotassium phosphate, 0.06% (w/v) of sodium phosphate dodeca-hydrate, 0.05% (w/v) of magnesium sulfate heptahydrate, and water was placed in 500-ml Erlenmeyer flasks in a respective amount of 100 ml, sterilized by autoclaving at 121° C. for 20 min, cooled and seeded with *Bacillus globisporus* C9, FERM BP-7143, followed by culturing under rotary-shaking conditions at 27° C. and 230 rpm for 48 hours for a seed culture. About 20 L of a fresh preparation of the same liquid culture medium as used in the above seed culture were placed in a 30 L fermentor, sterilized by heating, and then cooled to 27° C., and inoculated with 1% (v/v) of the seed culture, followed by culturing at 27° C. and pH 6.0 to 8.0 for 48 hours under aeration-agitation conditions. About 18 L of supernatant, obtained by centrifuging at 10,000 rpm for 30 min, had about 0.45 units/ml of α-isomaltosylglucosaccharide-forming enzyme activity, i.e., a total activity of about 8,110 units; 1.5 unit of α-isomaltosyl-transferring enzyme activity, i.e., a total enzymatic activity of about 26,900 units; and 0.95 unit/ml of cyclotetrasaccharide-forming activity, i.e., a total activity of about 17,100 units. The activities of enzymes were measured as follows:

The activity of α-isomaltosylglucosaccharide-forming enzyme was measured by the following assay: A substrate solution was prepared by dissolving maltotriose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 60 min. After stopping the reaction by boiling for 10 min, the amount of maltose formed with isomaltosylmaltose in the reaction mixture was determined by high-performance liquid chromatography (HPLC) according to the conventional method. One unit of α-isomaltosylglucosaccharide-forming activity was defined as the amount of the enzyme that forms one µmole of maltose per minute under the above conditions. The activity of α-isomaltosylglucosaccharide-forming enzyme is represented by the unit measured by the above assay throughout the specification.

The activity of α-isomaltosyl-transferring enzyme was measured by the following assay: A substrate solution was prepared by dissolving panose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 30 min. After stopping the reaction by boiling for 10 min, the amount of glucose formed with cyclotetrasaccharide in the reaction mixture was determined by the glucose oxidase-peroxidase method. One unit of α-isomaltosyl-transferring enzyme activity was defined as the amount of the enzyme that forms one µmole of glucose per minute under the above conditions. The activity of α-isomaltosyl-transferring enzyme is represented by the unit measured by the above assay throughout the specification.

Cyclotetrasaccharide-forming activity was measured by the following assay: A substrate solution was prepared by dissolving "PINE-DEX #100", a partial starch hydrolyzate commercialized by Matsutani Chemical Industry Co., Ltd., Hyogo, Japan, in 50 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 60 min. After stopping the reaction by boiling for 10 min, one ml of 50 mM acetate buffer (pH 5.0) containing 70 units/ml of "TRANSGLUCOSIDASE L AMANO™", an α-glucosidase produced by Amano Enzyme Inc., Nagoya, Japan, and 27 units/ml of glucoamylase, commercialized by Nagase Biochemicals, Ltd., Kyoto, Japan, was added to the reaction mixture and the resultant mixture was incubated at 50° C. for 60 min. After stopping the reaction by heating at 100° C. for 10 min, the amount of cyclotetrasaccharide was determined by a conventional HPLC method. One unit of cyclotetrasaccharide-forming activity was defined as the amount of enzyme that that forms one µmole of glucose per minute under the above conditions.

EXAMPLE A-2

Preparation of Enzymes Originated from *Bacillus globosporus* C9

About 18 L of the culture supernatant obtained in Example A-1 were salted out with 80% saturated ammonium sulfate solution and allowed to stand at 40° C. for 24 hours, and the formed precipitates were collected by centrifuging at 10,000 rpm for 30 min, dissolved in 10 mM sodium phosphate buffer (pH 7.5), and dialyzed against the same buffer to obtain about 400 ml of a crude enzyme solution. The crude enzyme solution had 8,110 units of α-isomaltosylglucosaccharide-forming enzyme, 24,700 units of α-isomaltosyl-transferring enzyme, and about 15,600 units of cyclotetrasaccharide-forming activity. The crude enzyme solution was subjected to ion-exchange column chromatography using 1,000 ml of "SEPABEADS FP-DA13" gel, an ion-exchange resin commercialized by Mitsubishi Chemical Industries, Ltd., Tokyo, Japan. Both α-isomaltosylglucosaccharide-forming enzyme and α-isomaltosyl-transferring enzyme and were eluted as non-adsorbed fractions without adsorbing on "SEPABEADS FP-DA13" gel. The fractions were collected and dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Bioscience K. K., Tokyo, Japan. Both enzymes adsorbed on "SEPHACRY HR S-200" gel and, when sequentially eluted with a linear gradient decreasing from 1 M to 0 M of ammonium sulfate and a linear gradient increasing from 0 mM to 100 mM of maltotetraose, α-isomaltosylglucosaccharide-forming enzyme and the α-isomaltosyl-transferring enzyme were separately eluted, i.e., the former was eluted with a linear gradient of maltotetraose at about 30 mM and the latter was eluted with a linear gradient of ammonium sulfate at about 0 M. Thus, fractions with the α-isomaltosylglucosaccharide-forming enzyme activity and those with the α-isomaltosyl-transferring enzyme activity were separately collected.

The followings describe the methods for purifying α-isomaltosylglucosaccharide-forming enzyme and α-isomaltosyl transferring enzyme, respectively.

EXAMPLE A-3

Purification of α-isomaltosylglucosaccharide-forming Enzyme Originated from *Bacillus globisporus* C9

The fractions comprising α-isomaltosylglucosaccharide-forming enzyme, obtained in Example A-2 was dialyzed against 10 mM sodium phosphate buffer (pH 7.0) with 1 M ammonium sulfate. The dialyzed solution was centrifuged to remove impurities, and subjected to hydrophobic column chromatography using 350 ml of "BUTYL-TOYOPEARL 650M" gel, a hydrophobic gel commercialized by Tosoh Corporation, Tokyo, Japan. The enzyme adsorbed on "BUTYL-TOYOPEARL 650M" gel and, when eluted with a linear gradient decreasing from 1 M to 0M of ammonium sulfate, the enzyme was eluted at an ammonium sulfate concentration of about 0.3 M, and fractions with the enzyme activity were collected. The collected solution was dialyzed against 10 mM sodium phosphate buffer (pH 7.0) with 1 M ammonium sulfate again. The dialyzed solution was centrifuged to remove impurities, and purified by affinity chromatography using "SEPHACRYL HR S-200" gel.

EXAMPLE A-4

Purification of α-isomaltosyl-transferring Enzyme Originated from *Bacillus globisporus* C9

The fractions comprising α-isomaltosyl-transferring enzyme, which are separated from those comprising α-isomaltosylgucosaccharide-forming enzyme by the affinity chromatography described in Example A-2, was dialyzed against 10 mM sodium phosphate buffer (pH 7.0) with 1 M ammonium sulfate. The dialyzed solution was centrifuged to remove impurities, and subjected to hydrophobic column chromatography using 350 ml of "BUTYL-TOYOPEARL 650M" gel, a hydrophobic gel commercialized by Tosoh Corporation, Tokyo, Japan. The enzyme adsorbed on "BUTYL-TOYOPEARL 650M" gel and, when eluted with a linear gradient decreasing from 1 M to 0M of ammonium sulfate, the enzyme was eluted at an ammonium sulfate concentration of about 0.3 M, and fractions with the enzyme activity was collected. The collected solution was dialyzed against 10 mM sodium phosphate buffer (pH 7.0) with 1 M ammonium sulfate again. The dialyzed solution was centrifuged to remove impurities, and purified by affinity chromatography using "SEPHACRYL HR S-200" gel.

The following describes a process for producing cyclotetrasaccharide as material of the present invention.

EXAMPLE B-1

Preparation of Cyclotetrasaccharide

A corn phytoglycogen, commercialized by Q.P. Corporation, Tokyo, Japan, was prepared into a 15% (w/v) solution, adjusted to pH 6.0 and at 30° C.; admixed with 1 unit/g-dry solid of purified α-isomaltosylglucosaccharide-forming enzyme, obtained in Example A-3, and 10 units/g-dry solid of purified α-isomaltosyl-transferring enzyme, obtained in Example A-4; incubated for 48 hours; and then heated at 100° C. for 10 min to inactivate enzymes. After adjusting the reaction mixture at pH 5.0 and 45° C., the remaining reducing oligosaccharides were hydrolyzed by α-glucosidase and glucoamylase as in the case of Example A-1. Then, the resulting reaction mixture was adjusted at pH 5.8 with sodium hydroxide and kept at 90° C. for one hour to inactivate enzymes. The resulting insoluble material was removed by filtration. After concentrating the resulting filtrate using a reverse osmosis membrane to give a concentration of about 16%, on a dry solid base, about 6.2 kg of a saccharide solution containing about 3,700 g of dry solid was obtained by decolorizing, deionizing, filtrating, and concentrating the solution according to the conventional manner.

The resulting saccharide solution was subjected to a column chromatography using about 225 liters of "AMBERLITE CR-1310 (Na-form)", an ion-exchanger resin commercialized by Japan Organo Co., Ltd., Tokyo, Japan, and fractionated under the conditions at a column temperature of 60° C. and a flow rate of about 45 L/hour. The fractions, showing cyclotetrasaccharide purity of 98% or higher by monitoring the saccharide composition of eluate by HPLC, were collected.

EXAMPLE B-2

Preparation of Hydrous Crystalline Cyclotetrasaccharide

The fractions containing cyclotetrasaccharide having a purity of about 98% or higher, which were obtained by the above method, were mixed and the resulting solution was concentrated to give a concentration of about 50%, on a dry solid basis, using a evaporator. Then, about five kilograms of the concentrated solution was placed in a cylindrical container and crystallized by cooling the temperature from 65° C. to 20° C. with taking a time of 20 hours, and white crystalline powder was obtained. Successively, 1,360 grams wet-weight of the crystalline material was collected by separating the massecuites with a centrifugal filtration apparatus. Further, 1,170 grams of crystalline cyclotetrasaccharide powder was obtained by drying the above crystalline material at 60° C. for three hours. The product showed an extremely high cyclotetrasaccharide purity of 99.9% or higher when sugar composition of the product was analyzed by HPLC. The crystalline powder showed a diffraction spectrum having major diffraction angles (2θ) of 10.1°, 15.2°, 20.3°, and 25.5° by X-ray diffraction analysis. Also, since the crystalline powder was found to have a moisture content of about 13.0% by the Karl-Fischer method, it was revealed that the crystalline powder was a crystal comprising 5-6 molecules of water per one molecule of cyclotetrasaccharide.

EXAMPLE B-3

Preparation of Anhydrous Crystalline Cyclotetrasaccharide

Crystalline cyclotetrasaccharide powder, obtained by the method of Example B-2, was dried in vacuo at 120° C. for 16 hours. The resulting crystalline powder showed a diffraction spectrum having major diffraction angles (2θ) of 10.8°, 14.7°, 15.0°, and 21.5° by X-ray diffraction analysis. Also, since the crystalline powder was found to have a moisture content of about 0.2% by the Karl-Fischer method, it was revealed that the crystalline powder was substantially in anhydrous form.

EXAMPLE B-4

Preparation of Anhydrous Cyclotetrasaccharide in Amorphous Form

The fractions containing cyclotetrasaccharide having a purity of about 98% or higher, which were obtained by the method of Example B-1, were mixed and the resulting solution was concentrated to give a concentration of 50%. After freezing the concentrated solution rapidly to −80° C., the resulting frozen material was dried by freeze-drying and further dried in vacuo at 80° C. for three hours, and the resulting dried material was pulverized using a pulverizer. The powder showed a diffraction spectrum having no peaks by X-ray diffraction analysis, suggesting the absence of crystal. Therefore, it was revealed that the powder was in amorphous form. Further, since the powder was found to have a moisture content of about 0.3% by the Karl-Fischer method, it was revealed that the powder was substantially in anhydrous form.

Cyclotetrasaccharide can be produced from starch by enzymatic reaction using enzymes, which are originated from microorganisms other than *Bacillus globisporus* C9 such as *Bacillus globisporus* C11 and N75, *Arthrobacter ramosus* S1, and *Arthrbacter globiformis* A19, as well as the procedures described above.

The following describes a process for producing the derivative of cyclotetrasaccharide of the present invention.

EXAMPLE C-1

Benzyl Derivative of Cyclotetrasaccharide

Five parts by weight of anhydrous crystalline cyclotetrasaccharide, obtained by the method of Example B-3, and 37 parts by weight of potassium hydroxide were dissolved in 64 parts by weight of benzyl chloride, and then the resulting solution was heated at 140° C. for three hours. After cooling the solution to the ambient temperature, 200 parts by weight of distilled water and 400 parts by weight of ethyl acetate were added to the solution and mixed. After standing the solution to separate aqueous phase and ethyl acetate phase, the resulting ethyl acetate phase was collected. After dehydrating the solution with suitable amount of anhydrous magnesium sulfate according to the conventional method, the solution was dried under a reduced pressure to obtain benzyl cyclotetrasaccharide.

It was revealed that the product had benzyl groups with an average degree of substitution of 7.3 by measuring the degree of substitution using a spectrophotometric analysis measuring the adsorption at 262 nm of benzene ring according to the conventional method. Since the product is a lipophilic substance, it can be advantageously incorporated into conventional oily cosmetics.

EXAMPLE C-2

Methyl Derivative of Cyclotetrasaccharide

Five parts by weight of anhydrous amorphous cyclotetrasaccharide, obtained by the method of Example B-4, was dissolved in 125 parts by weight of anhydrous dimethylsulfoxide, and then 12.5 parts by weight of sodium hydride was added to the solution and mixed. After cooling the solution for 10 min in an ice bath, it was heated at 60° C. for two hours. Successively, 22.5 parts by weight of methyl iodide was gradually added to the solution with cooling in an ice bath, and the resulting solution was stirred at the ambient temperature for 18 hours. After adding 40 parts by weight of methanol to the resulting solution, 200 parts by weight of distilled water was further added to the mixture. After adding 500 parts by weight of chloroform to the resulting solution and stirring, the mixture was stand to separate aqueous phase and chloroform phase, and then the chloroform phase was collected. After adding 50 parts by weight of distilled water to the chloroform solution, stirring, and standing, the resulting chloroform phase was collected again. After repeating the procedure ten times, the resulting solution was dehydrated with suitable amounts of anhydrous magnesium sulfate. After concentrating the solution, 100 parts by weight of saturated sodium chloride solution was added to the concentrate and the resulting solution was stirred at 60° C. for 30 min. After cooling the solution in an ice bath, the resulting supernatant (aqueous phase) was removed. The above procedure was repeated once again. The resultant was dissolved in 300 parts by weight of chloroform, stirred at 60° C. for 30 min, dehydrated with suitable amounts of anhydrous magnesium sulfate, and concentrated to obtain syrupy methyl cyclotetrasaccharide.

It was revealed that the product had methyl groups with an average degree of substitution of 7.5 by $^1$H-NMR analysis. Since the product is a lipophilic substance, it can be advantageously incorporated into conventional oily cosmetics.

EXAMPLE C-3

Linoleic Acid Ester of Cyclotetrasaccharide

Ten parts by weight of anhydrous crystalline cyclotetrasaccharide, obtained by the method of Example B-3, and 200 parts by weight of anhydrous pyridine were placed in a reaction vessel, and then four parts by weight of thiazolithion-linoleic acid amide, which is dissolved in five parts by weight of anhydrous pyridine, was further added to the solution under the ventilation of argon. The mixture was further admixed with 0.085 part by weight of 60% (w/w) oily sodium hydride and reacted at ambient temperature for two hours. After adding 1:5 parts by weight of saturated aqueous ammonium chloride solution, pyridine was removed under a reduced pressure, and 11.2 parts by weight of the residue was obtained. Then, the residue was purified using silica gel chromatography to obtain linolenic acid ester of cyclotetrasaccharide.

The product, having no taste or scent and a high activity, can be advantageously incorporated as a non-ionic surfactant into foods, cosmetics, and pharmaceuticals.

EXAMPLE C-4

Myristic Acid Ester of Cyclotetrasaccharide

Two hundred parts by weight of anhydrous amorphous cyclotetrasaccharide, obtained by the method of Example B-4, was dissolved in 800 parts by weight of N,N'-dimethylformamide, and 600 parts by weight of myristic acid methyl ester and four parts by weight of calcium carbonate were further added to the solution. The mixture was reacted with stirring at 85-95° C. for 24 hours under the reduced pressure of 100-200 mmHg. Successively, the reactant was evaporated to remove solvent, and the resulting residue was extracted two times using 300 parts by weight of acetone per once. After concentrating the extract and washing with benzene and ether, the resulting gummy oily substance was soaked into 300 parts by weight of acetone and extracted. The extract was cooled in an ice bath, and the resulting precipitate was collected and dried to obtain myristic acid ester of cyclotetrasaccharide.

The product, having no taste or scent and a high activity, can be advantageously incorporated as a non-ionic surfactant into foods, cosmetics, and pharmaceuticals.

EXAMPLE C-5

Dodecyl Ether of Cyclotetrasaccharide

After placing 390 parts by weight of n-dodecanol into a reaction vessel and heating to 125° C., one part by weight of p-toluene sulfonic acid as a catalyst was added to the solution, and then the pressure in the vessel was reduced to 5-10 mmHg. Separately, 100 parts by weight of anhydrous crystalline cyclotetrasaccharide, obtained by the method in Example B-3, was suspended in 130 parts by weight of n-dodecanol. The suspension was added into the above vessel drop by drop in a flow rate of 2.3 parts by weight/min with taking a time of 100 min for the reaction. Successively, the reactant was neutralized with aqueous sodium carbonate solution, and cyclotetrasaccharide dodecyl ether was obtained by evaporating residual alcohol.

The product having a high activity can be advantageously incorporated as a surfactant into conventional detergents such as detergent for washing, for kitchen, shampoo, and etc.

EXAMPLE C-6

Sulfate Ester of Cyclotetrasaccharide

After placing one part by weight of anhydrous crystalline cyclotetrasaccharide, obtained by the method of Example B-3, five parts by weight of sulfuric anhydride-dimethylformamide complex, separately prepared according to the conventional method, was added to the saccharide drop by drop and reacted at the ambient temperature for four hours and then further reacted at 70° C. for one hour. After neutralizing by adding suitable amount of 5 N sodium hydroxide solution, five-folds in volume of methanol was added to the solution and stood for a while. The resulting precipitate was collected by filtrating under a reduced pressure to obtain sulfate ester of cyclotetrasaccharide.

The product having a high quality can be advantageously incorporated into conventional cosmetics as a moisture-retaining agent and skin-care agent.

EXAMPLE C-7

Sulfate Ester of Cyclotetrasaccharide

One hundred parts by weight of anhydrous amorphous cyclotetrasaccharide, obtained by the method in Example B-4, was sulfated by the method of Example C-6, and a composition comprising sulfate ester of cyclotetrasaccharide was obtained.

The product having a high quality can be advantageously incorporated into conventional cosmetics as a moisture-retaining agent and skin-care agent.

EXAMPLE C-8

Cyanuric Acid Derivative of Cyclotetrasaccharide

Two parts by weight of anhydrous crystalline cyclotetrasaccharide, obtained by the method in Example B-3, was suspended in 20 parts by weight of N,N'-dimethylformamide, comprising a catalyst amount of pyridine and 5% (w/v) of cyanuric chloride, and reacted at the ambient temperature for three hours. The reaction mixture was filtrated, and the resulting residue was washed with acetone and dried to obtain cyanuric acid derivative of cycoltetrasaccharide.

The product can be bound with organic compounds such as proteins and nucleic acids.

EXAMPLE C-9

Tosyl-derivative of Cyclotetrasaccharide

Fifteen parts by weight of anhydrous crystalline cyclotetrasaccharide, obtained by the method in Example B-3, was suspended in 50 parts by weight of pyridine. Twelve parts by weight of p-toluene-sulfonylchloride was added to the suspension and stirred at 0° C. for 18 hours. The reactant was extracted with ethyl acetate, and the resulting extract was washed with diluted hydrochloric acid and brine. The washed extract was concentrated by drying to obtain tosyl-derivative of cyclotetrasaccharide.

The product is useful as an intermediate for various derivatives.

EXAMPLE C-10

Phenylsulfide Derivative of Cyclotetrasaccharide

Seven parts by weight of potassium t-butoxide was dissolved in 20 parts by weight of dimethylformamide, and seven parts by weight of thiophenol was further added drop by drop to the resulting solution under cooling to 0° C. and stirred at 0° C. for 10 min. Fourteen parts by weight of tosyl-derivative, prepared in Example C-9, was dissolved in dimethylformamide, added to the above solution, and stirred at the ambient temperature for one hour. The solution was extracted with ethyl acetate, and the resulting extract was washed with brine. Then, the washed extract was concentrated. The resulting residue (concentrate) was purified by silica gel chromatography to obtain phenylsulfide derivative of cyclotetrasaccharide.

The product is a lipophilic substance and can be used to cosmetics and pharmaceuticals.

EXAMPLE C-11

Amino Derivative of Cyclotetrasaccharide

Ten parts by weight of tosyl-derivative of cyclotetrasaccharide, prepared in Example C-9, was dissolved in 20 parts by weight of anhydrous dimethylformamide in the presence of nitrogen gas. One part by weight of anhydrous sodium azide was further added to the solution, and the resulting mixture was stirred at 65° C. for 18 hours in the presence of nitrogen gas. After cooling the solution to the ambient temperature, 150 parts by weight of water cooled with ice was added to the solution. The resulting precipitate was collected and dried to obtain diazo-derivative. Successively, one part by weight of the diazo-derivative was dissolved in the mixture of 100 parts by weight of purified dioxane and 20 parts by weight of distilled methanol. Four parts by weight of purified triphenylphosphine was added to the solution while stirring in the presence of nitrogen gas and further stirred for one hour. Then, five parts by weight of concentrated aqueous ammonia was added drop by drop to the above solution and the resultant was stirred for 12 hours in the presence of nitrogen gas. After evaporating the solvent, the product was suspended in 250 parts by weight of water, and the pH of the solution was set to pH 4 with 1 N hydrochloric acid. The suspension was washed three-times with 500 parts by weight of benzene to remove triphenylphosphineoxide. The resultant was freeze-dried to obtain amino derivative of cyclotetrasaccharide.

The product has an ability to bind with organic compounds having carboxyl groups and can be useful as an intermediate for introducing other substituents.

The present inventors deposited *Bacillus globisporus* C9 (FERM BP-7143), described in the present specification, on Apr. 25, 2000, in International Patent Organism Depositary National Institute of Advanced Industrial Science and Technology, Tsukuba Central 6, 1-1, Higashi 1-Chome Tsukuba-shi, Ibaraki-ken, 305-8566, Japan. The present inventors also deposited *Bacillus globisporus* C11 (FERM BP-7144), described in the present specification, on Apr. 25, 2000, in International Patent Organism Depositary National Institute of Advanced Industrial Science and Technology, Tsukuba Central 6, 1-1, Higashi 1-Chome Tsukuba-shi, Ibaraki-ken, 305-8566, Japan. The present inventors also deposited *Bacillus globisporus* N75 (FERM BP-7591), described in the present specification, on May 16, 2001, in International Patent Organism Depositary National Institute of Advanced Industrial Science and Technology, Tsukuba Central 6, 1-1, Higashi 1-Chome Tsukuba-shi, Ibaraki-ken, 305-8566, Japan. The present inventors also deposited *Arthrobacter globiformis* A19 (FERM BP-7590), described in the present specification, on May 16, 2001, in International Patent Organism Depositary National Institute of Advanced Industrial Science and Technology, Tsukuba Central 6, 1-1, Higashi 1-Chome Tsukuba-shi, Ibaraki-ken, 305-8566, Japan. The present inventors also deposited *Arthrobacter ramosus* S1 (FERM BP-7592), described in the present specification, on May 16, 2001, in International Patent Organism Depositary National Institute of Advanced Industrial Science and Technology, Tsukuba Central 6, 1-1, Higashi 1-Chome Tsukuba-shi, Ibaraki-ken, 305-8566, Japan.

INDUSTRIAL APPLICABILITY

As described above, the derivatives of cyclotetrasaccharide of the present invention are quite novel compounds, having substituents which could not be obtained by the conventional enzymatic reaction systems, and which are synthesized by reacting reactive reagents with cyclotetrasaccharide. Therefore, since the physical properties of cyclotetrasaccharide can be freely changed by the modification, novel uses of cyclotetrasaccharide, which has been impossible, can be provided. Therefor, the derivatives of cyclotetrasaccharide of the present invention can be used intact as detergents, moisture-retaining agents, and skin-care agents by incorporating into foods, cosmetics, and pharmaceuticals. Also, novel organic compounds can be obtained by binding cyclotetrasaccharide with the same or other compounds. Physical properties of cyclotetrasaccharide could be imparted to other compounds by binding cyclotetrasaccharide with them.

The invention claimed is:

1. A derivative of cyclic tetrasaccharide, which has a structure represented by Formula 1:

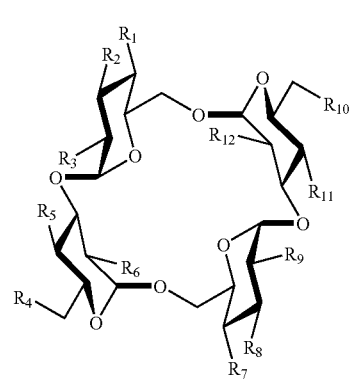

Formula 1 wherein $R_1$ to $R_{12}$ means a hydroxyl group or a substituent excluding a hydroxyl group selected from the group consisting of aliphatic hydrocarbon groups having 1-18 carbon atoms, aliphatic cyclic hydrocarbon groups, mono- or polycyclic aromatic hydrocarbon groups, saturated, unsaturated, branched or linear fatty acid ester groups, carboxylic acid ester groups, sulfuric ester groups, phosphoric ester groups, alkoxyl groups having 1-18 carbon atoms, aromatic alcohol ether groups, carboxyl groups, ketone groups, amino groups, hydroxylamino groups, oxime groups, carbamide groups, carbamic acid ester groups, thiocarbamic acid O-ester groups, thiocarbamic acid S-ester groups, imino groups, azirine groups, nitro groups, nitroso groups, azide groups, nitrile groups, isonitrile groups, cyano groups, isocyano groups, isothiocyanate groups, mercapto groups, sulfonyl groups, sulfonic acid groups, sulfoxide groups, sulfonyl imido groups, p-toluene sulfonyl groups, and halogen groups; but at least one of $R_1$ to $R_{12}$ is substituted with said substituent excluding a hydroxyl group.

2. The derivative of cyclic tetrasaccharide of claim 1, which has an average degree of substitution of one or more.

3. A process for producing a derivative of cyclic tetrasaccharide of claim 1, which comprises a step of:

allowing a reactive reagent to act on a cyclic tetrasaccharide represented by Chemical formula 1 thereby substituting one or more substituents in $R_1$ to $R_{12}$ in Formula 1 with substituents selected from the group consisting of aliphatic hydrocarbon groups having 1-18 carbon atoms, aliphatic cyclic hydrocarbon groups, monmo- or polycyclic aromatic hydrocarbon groups, saturated, unsaturated, branched or linear fatty acid ester groups, carboxylic acid ester groups, sulfuric ester groups, phosphoric ester groups, alkoxyl groups having 1-18 carbon atoms, aromatic alcohol ether groups, carboxyl groups, ketone groups, amino groups, hydroxylamino groups, oxime groups, carbamide groups, carbamic acid ester groups, thiocarbamic acid O-ester groups, thiocarbamic acid S-ester groups, imino groups, azirine groups, nitro groups, nitroso groups, azide groups, nitrile groups, isonitrile groups, cyano groups, isocyano groups, isothiocyanate groups, mercapto groups, sulfonyl groups, sulfonic acid groups, sulfoxide groups, sulfonyl imido groups, p-toluene sulfonyl groups, and halogen groups:

Chemical formula 1

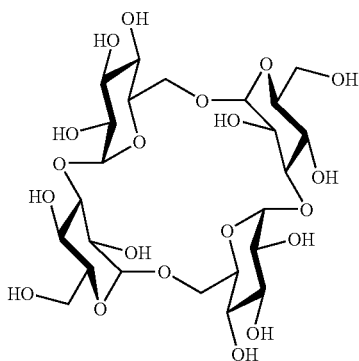

4. The process of claim 3, wherein said cyclic tetrasaccharide is in an anhydrous form.

5. The process of claim 3 or 4, wherein said reactive reagent is one or more reagents selected from the group consisting of acids, bases, alcohols, ketones, halogens, amines, cyanogens, nitriles, oxyranes, isocyanates, isothiocyanates, thiols, sulfones, and their reactive derivatives.

6. The process of any one of claims 3 to 5, wherein said cyclic tetrasaccharide represented by Chemical formula 1 is produced by allowing enzymes to act on starch:

Chemical formula 1

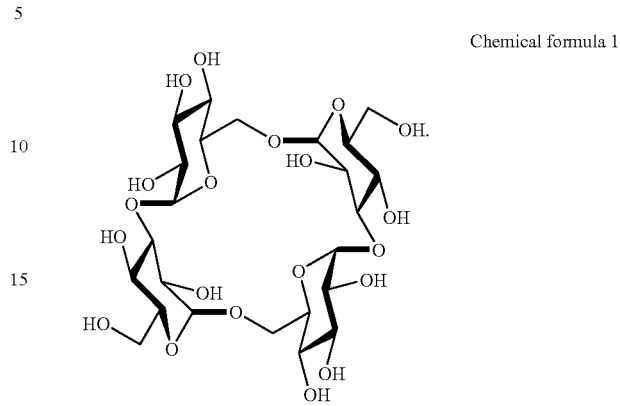

7. A composition comprising the derivative of cyclic tetrasaccharide of claim 1.

* * * * *

UNITED STATES PATENT AND TRADEMARK OFFICE
CERTIFICATE OF CORRECTION

PATENT NO.        : 7,375,095 B2                                    Page 1 of 1
APPLICATION NO.   : 10/495975
DATED             : May 20, 2008
INVENTOR(S)       : Kazuyuki Oku et al.

It is certified that error appears in the above-identified patent and that said Letters Patent is hereby corrected as shown below:

On the Title page item (73),

ASSIGNEE NAME, "Kabashiki Kaisha Hayashibara Seibutsu Kagaku" should read --KABUSHIKI KAISHA HAYASHIBARA SEIBUTSU KAGAKU--

Signed and Sealed this

Fifteenth Day of July, 2008

JON W. DUDAS
*Director of the United States Patent and Trademark Office*